(12) United States Patent
Sancho Sanz et al.

(10) Patent No.: US 8,461,202 B2
(45) Date of Patent: Jun. 11, 2013

(54) COMPOSITION FOR TREATING INFECTIOUS DISEASES

(75) Inventors: Javier Sancho Sanz, Zaragoza (ES); Adrián Velazquez Campoy, Zaragoza (ES); Nunilo Cremades Casasin, Zaragoza (ES)

(73) Assignee: Universidad de Zaragoza, Zaragoza (ES)

( * ) Notice: Subject to any disclaimer, the term of this patent is extended or adjusted under 35 U.S.C. 154(b) by 647 days.

(21) Appl. No.: 12/529,626

(22) PCT Filed: Feb. 22, 2008

(86) PCT No.: PCT/ES2008/000098
§ 371 (c)(1),
(2), (4) Date: Nov. 3, 2009

(87) PCT Pub. No.: WO2008/107502
PCT Pub. Date: Sep. 12, 2008

(65) Prior Publication Data
US 2010/0087690 A1    Apr. 8, 2010

(30) Foreign Application Priority Data
Mar. 2, 2007 (ES) .................................. 200700645

(51) Int. Cl.
*A01N 37/00* (2006.01)
*A01N 37/10* (2006.01)
*A01N 33/02* (2006.01)

(52) U.S. Cl.
USPC ........................... 514/557; 514/570; 514/647

(58) Field of Classification Search
USPC ......................................... 514/557, 570, 647
See application file for complete search history.

(56) References Cited

U.S. PATENT DOCUMENTS

| | | | |
|---|---|---|---|
| 3,394,191 A | 7/1968 | Oftedahl | |
| 3,629,465 A | 12/1971 | Manowitz et al. | |
| 3,985,761 A | 10/1976 | Somasekhara et al. | |
| 5,763,470 A | 6/1998 | Tang et al. | |
| 6,749,645 B2 | 6/2004 | Pasquier et al. | |
| 2004/0167189 A1 | 8/2004 | Bulavin et al. | |
| 2005/0187268 A1 | 8/2005 | Von Rechenberg et al. | |
| 2005/0282818 A1 | 12/2005 | Ramesh et al. | |
| 2006/0247284 A1 | 11/2006 | Caccuri et al. | |

FOREIGN PATENT DOCUMENTS

| | | |
|---|---|---|
| WO | WO 8803147 | 5/1988 |
| WO | WO 9640110 | 12/1996 |
| WO | WO 9723626 | 7/1997 |
| WO | WO 0035856 | 6/2000 |
| WO | WO2004/046081 | 6/2004 |
| WO | WO 2005/019177 A1 * | 3/2005 |
| WO | WO2005082341 | 9/2005 |

OTHER PUBLICATIONS

Belton J.G.: 'A novel N-S oxygen migration in 2,1,3-benzoxadiazole systems' Proceedings of the Royal Irish Academy. Section B: Biological, Geological and Chemical Science vol. 74, No. 14, pp. 185-192.
Beteringhe A. et al.: 'QSPR study for the hydrophobicity of 4-aryloxy-7-nitrobenzofurazan and 2-aryloxy-(alfa-acetyl)-phenoxathiin derivatives' Internet Electronic Journal of Molecular Design vol. 5, 2006, pp. 237-246.
Whitehouse M.W. et al.: '4-nitrobenzofurazans and 4-nitrobenzofuroxans: a new class of thiol-neutralising agents and potent inhibitors of nucleic acid synthesis in leucocytes' Biochemical Pharmacology vol. 17, No. 1, 1968, pp. 158-161.
Ghosh P.B. et al.: 'Potential antileukemic and immunosuppressive drugs. Preparation and in vitro pharmacological activity of some benzo-2,1,3-oxadiazoles (benzofurazans) and their N-oxides (benzofuroxans)' J. Med. Chem. vol. 11, No. 2, 1968, pp. 305-311.
Bem M. et al.: 'Synthesis of 4-(4'-formylaryloxy)-7-nitrobenzofurazan derivatives from 4-chloro-7-nitrobenzofurazan and some formyiphenols in the presence of crown ethers' Revue Roumaine de Chimie, 2003, vol. 48, No. 5, pp. 387-392.
Cremades et al.: 'Discovery of Specific Flavodoxin Inhibitors as Potential Therapeutic Agents against *Helicobacter pylori* Infection', ACS Chemical Biology vol. 4, No. 1, pp. 928-938, published online Sep. 2, 2009.
Freigang et al.: 'Crystal structure of oxidized flavodoxin, an essential protein in *Helicobacter pylori*', Protein Science, 2002, 11, pp. 253-261.
Definition for "Infectious Disease" [retrieved May 15, 2011]. Retrieved from the Internet: http://www.merriam-webster.com/medical/infectious+disease?show=0&t-1305401385.
Maybridge Registry for compound No. RN882289-31-8, Apr. 30, 2006.
European Search Report dated Jan. 6, 2012 issued for European Patent Application No. 08750368.6.
Belton J.G.: 'A novel N-S oxygen migration in 2,1,3-benzoxadiazole systems' Proceedings of the Royal Irish Academy. Section B: Biological, Geological and Chemical Science vol. 74, No. 14, Aug. 7, 1974, pp. 185-192.

* cited by examiner

*Primary Examiner* — Jafar Parsa
(74) *Attorney, Agent, or Firm* — K&L Gates LLP

(57) ABSTRACT

Compounds of the general formula (I) or salts thereof, for use as a pharmaceutical composition for treating infectious diseases, especially for treating diseases caused by *Helicobacter* are disclosed. $R_1$ is an H atom, an X atom or a $CX_mH_{3-m}$ radical wherein each X can be the same or different and is a halogen selected from F, Cl, Br or I, and m is an integer between 1 and 3; $R_2$ is an $NO_2$ group, a COOR' group or an $SO_3R'$ group; R' is a hydrogen (H) atom or a $C_1$-$C_6$ alkyl group; and n is an integer between 1 and 5.

11 Claims, 1 Drawing Sheet

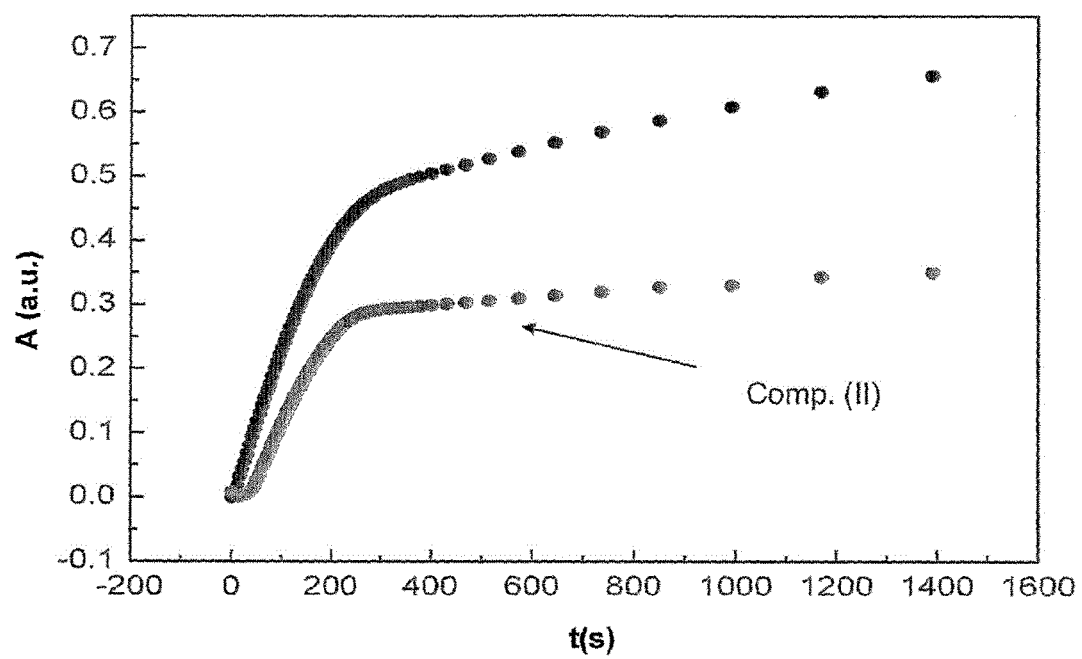

COMPOSITION FOR TREATING INFECTIOUS DISEASES

CROSS REFERENCE TO RELATED APPLICATIONS AND PRIORITY CLAIM

This application claims the benefit under 35 U.S.C. §371 to PCT/ES2008/000098 filed Feb. 22, 2008, which claims the benefit of Spanish Patent Application No. P200700645 filed Mar. 2, 2007 in Spain. The entire disclosures of said applications are incorporated herein by reference thereto.

BACKGROUND

1. Technical Field

The present disclosure relates to a compound, capable of inhibiting flavodoxin, of the general formula shown in (I), for its use as a pharmaceutical composition for the treatment of infectious diseases, more specifically those caused by *Helicobacter*.

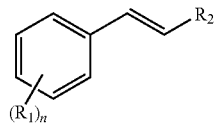

(I)

2. Background

Infection by *Helicobacter pylori* (*H. pylori*) is one of today's most common chronic diseases; in fact this bacterium is found to colonise the gastric mucosa of more than 50% of the human population.

*H. pylori* is a gram-negative *bacillus* that causes chronic gastritis, gastric and duodenal ulcers and is a risk factor in the development of MALT lymphoma and adenocarcinoma (one of the most frequent and lethal types of cancer).

The conventional treatment used to eradicate *Helicobacter pylori* infection consists of two broad spectrum antibiotics and a proton pump inhibitor. Therefore there is no specific treatment for this condition nor is the current treatment particularly effective as the proportion of successfully treated patients does not exceed 80%. In addition, the high mutational variability is causing a decline in conventional treatment efficiency due to a growing increase in resistance to conventional antibiotics.

BRIEF DESCRIPTION OF THE FIGURE

FIG. 1 shows a graph comparing the product formation curves in the essential reaction of *H. pylori* in the presence and absence of the compound of the formula shown in (II) at a concentration of 50 μM. Measurement of the absorbance (A) (AU is the unit of absorbance) at 340 nm against time (t) in seconds (s).

DETAILED DESCRIPTION OF THE PREFERRED EMBODIMENTS

New compounds for use as pharmaceutical compositions are described herein. In addition, the present disclosure describes the use of these compositions for the treatment of infectious diseases, and more specifically, diseases caused by *H. pylori*.

A "pharmaceutical composition" is understood to be a medication.

Therefore, a first aspect of the present disclosure relates to the use of compounds (hereinafter "disclosed compounds"), the general formula of which is shown in (I):

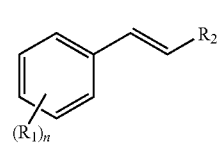

(I)

or any of its salts for use as a pharmaceutical composition, where $R_1$ and n are defined as follows:

$R_1$ is an atom of hydrogen (H), halogen (X), or a radical of the general type $CX_mH_{3-m}$; where X is a halogen that can be selected from fluorine (F), chlorine (Cl), bromine (Br) and iodine (I), preferably X is F or Cl, and more preferably X is F.

m indicates the number of possible halogen atoms, and takes values of between 1 and 3. When m is 2 or 3, X can be atoms of the same halogen or different, and are selected from the group previously cited. Preferably m is 3, that is a trihalide ($CX_3$) and more preferably $CF_3$.

n indicates the number of substituents of the aromatic ring and takes values of 1 to 5, preferably 1, 2 or 3. More preferably, n is 2.

$R_2$ is a group selected from the radicals $NO_2$, COOR' and $SO_3R'$, where R' is a hydrogen atom (H) or a $C_1$-$C_6$ alkyl group. Preferably $R_2$ is a $NO_2$, COOH or $SO_3H$ group; more preferably $NO_2$.

The alkyl $C_1$-$C_6$ group can be linear or ramified, preferably it is an alkyl $C_1$-$C_4$ group such as, but without limitation, a methyl, ethyl, propyl, iso-propyl, ter-butyl and more preferably, a non-substituted alkyl group.

In a preferred embodiment, a disclosed compound has the following formula (II):

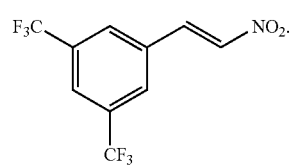

(II)

Another aspect of the present disclosure comprises the use of the compounds with the general formula shown in (I) for the preparation of a pharmaceutical composition. This composition is used for the treatment of infectious diseases.

Some infectious diseases are caused by gram negative bacteria, such as in the case of the *Helicobacter* bacterium.

An effective therapeutic target for the treatment of these particular types of diseases is flavodoxin, which is a redox protein, of structure α/β, the function of which is electron transfer in a variety of metabolic pathways. In *Helicobacter pylori*, it accepts electrons from the enzyme pyruvate:flavodoxin oxidoreductase (PFOR) in the pyruvate oxidative decarboxylation pathway to convert pyruvate into acetyl CoA. To perform its function as an electron mediator, flavodoxin carries a flavin mononucleotide (FMN) molecule bound non-covalently. In spite of its structural similarity to flavodoxins of other species, that of *H. pylori* presents a very significant difference in the FMN binding site, where a residue of alanine replaces the tryptophan that is characteristic of the other flavodoxins. For this reason it presents a weakness adjacent to the cofactor binding site, which is an appropriate site for the binding of molecules that are potential inhibitors of its biological activity, either because they alter the FMN redox potential inhibiting electron transfer to PFOR, or simply because they block the coupling of the two proteins. Blocking the pyruvate oxidation pathway determines the death of the bacterium.

Flavodoxin is therefore essential for the survival of the bacterium and is absent in humans and, as described previously, constitutes a therapeutically suitable target for the eradication of diseases related with the infection.

It has been demonstrated (see examples) that the compounds of the invention completely inhibit the *H. pylori* bacteria in the micro molar concentration range by the inhibition of pyruvate oxidation in which *H. pylori* flavodoxin participates.

Therefore, a preferred embodiment comprises the use of the compounds of the general formula shown in (I) for the treatment of infectious diseases caused by bacteria of the genus *Helicobacter*, preferably of the species *Helicobacter pylori*.

These compounds, therefore, can be used in the preparation of a medication or pharmaceutical composition for the treatment of these diseases. The pharmaceutical composition, in addition to these compounds, may comprise pharmaceutically acceptable excipients, additives, etc.

Therefore these compounds able to inhibit flavodoxin constitute a very good alternative to the treatment of infectious diseases, particularly those caused by *Helicobacter*, more specifically by *H. pylori*.

The use of compounds with the general formula shown in (I), described herein, will make up for the absence of a specific treatment against this pathogen as these compounds are specific inhibitors of the flavodoxin protein. Also, the absence of a homologous protein in humans makes these inhibitors to be a specific molecular therapy with no or low secondary effects on the host organism.

Infectious diseases caused by *Helicobacter pylori* are related to gastrointestinal pathologies such as chronic gastritis, gastric or duodenal ulcers, lymphoma and gastric cancer. Therefore, a more preferred embodiment comprises the use of the disclosed compounds for the treatment of infectious diseases such as chronic gastritis, gastric and/or duodenal ulcers, lymphoma and gastric cancer.

Throughout the description and the claims, the word "comprise" and its variants does not intend to exclude other technical characteristics, additives, components or steps. For experts in the field, other objects, advantages and characteristics of the invention will become apparent from the disclosure. The following examples and figures are provided by way of illustration and are not intended to be limiting.

The specificity and effectiveness of the flavodoxin inhibitors described herein are illustrated below by means of trials carried out by the inventors. The following examples are for illustrative purposes only and are not intended, nor should they be interpreted, to limit the scope of the claims.

EXAMPLES

Example 1

Cloning the Gene for Recombinant Flavodoxin

The *H. pylori* genomic DNA was isolated from antigen-positive patients using the QIAamp DNA Stool Mini Kit (Qiagen).

The DNA sequence coding for flavodoxin was amplified by PCR using the restriction enzyme Nco (SEQ ID No. 1) and the restriction enzyme BamHI (SEQ ID No. 2) and Taq DNA polymerase (Madgen).

After amplification, fragments of some 600 nucleotides were detected corresponding to the fragment of the flavodoxin gene (613 nucleotides).

The fragments were purified and cloned into the NcoI-BamHI sites of the pET28a (Novagen) expression vector using standard techniques. The insertion of the gene and its direction and integrity were checked by DNA sequencing of the plasmid using the bacteriophage T7 promoter.

Example 2

Expression and Purification of *H. pylori* Recombinant Flavodoxin

*E. coli* BL21 competent cells were transformed with the pET28a plasmid containing the insert and were cultivated in 10 ml of Luria-Bertani medium in the presence of kanamycin (30 μg/mL) at 37° C.

The culture was diluted 10 times in the same conditions and allowed to grow until the optical density was 0.8 at 600 nm. They were induced with IPTG (final concentration 1 mM) and the cells were allowed to grow for 3-4 hours.

After this time, the culture was centrifuged to obtain the cells, which were washed with 0.15 M NaCl.

After centrifugation, the cells were resuspended in 50 mM Tris-HCl buffer, pH 8, 1 mM β-mercaptoethanol, 1 mM EDTA and 1 mM PMSF.

The cells were ruptured with cycles of ultrasound and the cell debris were eliminated by centrifugation (45 min at 18,000 rpm at 4° C.).

The crude extract obtained was precipitated with 65% of saturated ammonium sulphate and was centrifuged. The supernatant was loaded on a DEAE DE-52 cellulose column equilibrated with 50 mM Tris-HCl, pH 8, at 65% ammonium sulphate.

The protein eluted with a reverse gradient of 65 to 0% of $(NH_4)_2SO_4$ saturation.

After dialysis of the protein with 50 mM Tris-HCl buffer, pH 8, it was loaded on another DEAE DE-52 cellulose column equilibrated in the same buffer.

The protein was eluted by a gradient of 0 to 1 M NaCl. The pure protein was obtained after this column, although to separate the apo-form (without cofactor) and the holo-form (with cofactor) of the protein, it is necessary to pass the sample through a MonoQ 10/10 column in a FPLC system.

The protein was stored at −20° C.

Example 3

Inhibition Tests

Flavodoxin is an essential protein for *Helicobacter pylori* survival as it participates in a fundamental reaction for obtaining energy from the oxidative decarboxylation of pyruvate. In this reaction, flavodoxin transfers electrons between the PFOR enzyme and the FqrB enzyme, which releases them to $NADP^+$.

In the following example, the cDNA corresponding to the gene of the PFOR enzyme inserted into the pBS(KS) vector and the gene of the FqrB enzyme inserted into the pET29b vector were used.

Both recombinant enzymes are expressed as a soluble fraction, PFOR in *E. coli* JVQ2 competent cells that are deficient in reductases (nsfA and nfsB) and FqrB in BL21(DE3) competent cells.

The cells grow in LB medium at 37° C. and are selected by their resistance to ampicillin in the case of JVQ2 and kanamycin in the case of BL21.

Then they were induced with IPTG and after 3 hours of induction (the optical density is around 0.8), they were stored at −80° C.

The FqrB enzyme is expressed with a tail of 6 histidine residues at the N-terminal of the amino acid sequence in order to be purified by nickel affinity chromatography. Thus, the cells were resuspended in the rupture buffer (50 mM sodium phosphate, 300 mM NaCl, pH 8 with 10 mM imidazole) and ruptured by cycles of ultrasound of 10 seconds, resting 1 minute between each cycle.

The remains of the cells were eliminated by centrifugation at 10,000 rpm for 30 min at 4° C. and the supernatant was loaded on a nickel affinity column (Ni-NTA agarose, Qiagen) that had been previously equilibrated with the rupture buffer. Three washes were performed with 20, 40 and 60 mM imidazole to eliminate non-specific interactions of the matrix with other proteins and the FqrB enzyme was eluted from the column with a gradient of 250 mM imidazole.

Lastly, the enzyme was dialysed in the PBS storage buffer with 10% glycerol. For the enzyme tests, the histidine tail was not removed as it was seen that it did not affect the activity.

The PFOR enzyme is inactivated by exposure to air (inactivated by the oxygen), and so it was purified in a system where a flow of nitrogen had been previously passed, and the connections were hermetically sealed.

The cells were resuspended in 50 mM Tris-HCl, pH 7.4 with 1 mM MgCl, 1 mM DTT and 10% glycerol, sonicated with cycles of ultrasound of 10 seconds resting 1 minute between the cycles and centrifuged at 8,000 rpm for 10 min at 4° C. to eliminate the cell debris. It was then centrifuged at higher speed (2 h at 24,000 rpm) and the concentration of protein was determined by the Bradford assay.

The crude extract was diluted with the previous buffer until the protein concentration was 25 mg/mL. The protein was partially purified in a DEAE DE-52 column with a gradient of 0-0.5 M sodium chloride. The fractions containing the enzyme were located by a rapid assay in aerobic conditions that consisted of adding 25 µL reaction buffer (500 mM pyruvate, 10 mM CoA and 100 mM benzyl viologen) to 50-100 µL fractions, and the fractions containing the enzyme changed color from colorless to blue.

Then, the fractions containing the enzyme were dialysed in the storage buffer (the same that was used to resuspend the cells). Subsequent purification steps reduced the yield considerably, and as the specific enzyme activity was not seen to be altered by impurities, for these tests the enzyme was partially purified as explained above.

The sequential reaction of electron transfer between pyruvate, PFOR, flavodoxin, FqrB and $NADP^+$ (activity assay) was followed spectroscopically by the appearance of the signal at 340 nm with the formation of NADPH. The reaction mixture contained 100 mM potassium phosphate pH 7, 10 mM pyruvate, 0.18 mM CoA, 1 mM MgCl, 0.3 mM $NADP^+$, 0.09 mg/ml PFOR, 10 µM Fld and 0.15 µM FqrB. The mixture, except CoA, was placed in a cuvette specially designed for anaerobic conditions. Oxygen was removed by means of 5 minute cycles with alternate flows of vacuum and argon. The reaction was started by the addition of 0.18 mM coenzyme A (CoA) that was held in a compartment inside the same cuvette. The reaction completed 15 minutes after adding the CoA reagent. The omission of any one of the reaction components resulted in absence of NADPH formation, indicating that all the components were essential and irreplaceable for the transfer of electrons between pyruvate and $NADP+$.

The inhibition assays were carried out in the same conditions as the activity assays previously described, adding an additional 50 µM of the disclosed compound of the general formula shown in (II) to the reaction cuvette.

As shown in FIG. 1, the inhibition was almost total at this concentration.

Example 4

Binding Energy of the Inhibitors

The specific binding of the inhibitors of the present invention to flavodoxin of *H. pylori* was confirmed by isothermal titration calorimetry (ITC). This technique not only measures the affinity of each compound for the target protein, but also determines the contribution of the enthalpic and entropic components of binding.

The binding experiments were carried out in 50 mM EPPS buffer, pH 9 with 7% DMSO, with the inhibitor in the injection syringe at a concentration of 300-500 µM, and the protein around 20 µM in the measurement cell.

The affinity constant of the inhibitors was around 1 µM, in agreement with the results obtained in the inhibition assays (they completely inhibit the decarboxylation of pyruvate at micromolar concentrations).

In particular, the compound of the general formula shown in (II) has an affinity for flavodoxin of 8.0 (±2.0) µM.

Having sufficiently described the nature of the various example embodiments, it should be stated that the aforementioned compounds and those represented in the drawings may have their details modified provided it does not alter the fundamental principle.

The invention is, of course, not limited to the examples described but cover all the variants defined in the claims. The terms "a" and "an" and "the" and similar referents used in the context of the following claims are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g. "such as") provided herein is intended merely to better illuminate the embodiments and does not pose a limitation on the scope of the embodiments otherwise claimed. No language in the specification should be construed as indicating any non-claimed element essential to the practice of the embodiments.

The use of the term "or" in the claims is used to mean "and/or" unless explicitly indicated to refer to alternatives only or the alternatives are mutually exclusive, although the disclosure supports a definition that refers to only alternatives and "and/or." Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments are described herein, including the best mode known to the inventors for carrying out the invention. Of course, variations on those preferred embodiments will become apparent to those of ordinary skill in the art upon reading the foregoing description. The inventors expect those of ordinary skill in the art to employ such variations as appropriate, and the inventors intend for the embodiments to be practiced otherwise than specifically described herein. Accordingly, these embodiments include all modifications and equivalents of the subject matter recited in the claims appended hereto as permitted by applicable law. Moreover, any combination of the above-described elements in all possible variations thereof are encompassed by the embodiments unless otherwise indicated herein or otherwise clearly contradicted by context.

Further, it is to be understood that the example embodiments disclosed herein are illustrative. Other modifications that may be employed are within the scope of the embodiments. Thus, by way of example, but not of limitation, alternative configurations of the present embodiments may be utilized in accordance with the teachings herein. Accordingly, the present embodiments are not limited to that precisely as shown and described in the specification and drawings.

The invention claimed is:

1. A method of treating an infectious disease caused by bacteria comprising administering to a patient in need thereof a pharmaceutical composition, wherein said composition comprises a compound of the general formula shown in (I) or any of its salts,

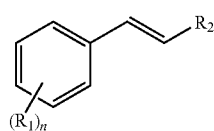

(I)

wherein:
R$_1$ is an atom of H, X or a CX$_m$H$_{3-m}$ radical; X represents a halogen selected from F, Cl, Br and I; and they can be the same or different, m takes values from 1 to 3;

R$_2$ is a NO$_2$, COOR' or SO$_3$R' group; R' represents a hydrogen atom (H) or a C$_1$-C$_6$ alkyl group; and n is from 1 to 5.

2. The method according to claim 1, wherein the infectious disease is caused by *Helicobacter*.

3. The method according to claim 1, wherein the infectious disease is caused by *Helicobacter pylori*.

4. The method according to claim 1, wherein the infectious disease caused by bacteria is gastritis.

5. The method according to claim 1, wherein the infectious disease caused by bacteria is gastroduodenal ulcer.

6. The method according to claim 1, wherein the infectious disease caused by bacteria is lymphoma.

7. The method according to claim 1, wherein the infectious disease caused by bacteria is gastric cancer.

8. The method according to claim 1, wherein n takes values from 1 to 3, R$_1$ is a CX$_m$H$_{3-m}$ radical where X is F or Cl and R$_2$ is a NO$_2$, COOH or SO$_3$H group.

9. The method according to claim 8, wherein n is 2 and m is 3 and R$_2$ is NO$_2$.

10. The method according to claim 9, wherein X is F.

11. The method according to claim 1, wherein said compound is the formula (II):

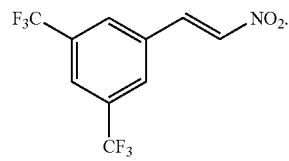

(II)

* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial sequence
<220> FEATURE:
<223> OTHER INFORMATION: Primer Nco-

<400> SEQUENCE: 1
ggattgagca tatgggaaaa attgg                                          25

<210> SEQ ID NO 2
<211> LENGTH: 25
<212> TYPE: DNA
<213> ORGANISM: Artificial sequence
<220> FEATURE:
<223> OTHER INFORMATION: Primer BamHI

<400> SEQUENCE: 2
gatcttaacc taggaagtaa caatc                                          25
```